United States Patent [19]

Micetich et al.

[11] 4,091,026
[45] May 23, 1978

[54] THIAZOLENEAZETIDINONES FROM DITHIAZENEAZETIDINONES

[75] Inventors: Ronald G. Micetich; Clinton G. Chin, both of Edmonton, Canada; Robert B. Morin, Warren, N.J.

[73] Assignee: Connlab Holdings Limited, Canada

[21] Appl. No.: 622,627

[22] Filed: Oct. 15, 1975

[51] Int. Cl.$^2$ ............................................. C07D 513/04
[52] U.S. Cl. ........................... 260/306.7 C; 260/239.1; 260/239 A; 544/18; 544/30; 544/5; 544/21; 544/28; 544/29; 544/30
[58] Field of Search .................... 260/243 R, 306.7 R, 260/243 C, 306.7 C

[56] References Cited
U.S. PATENT DOCUMENTS

| 3,560,483 | 2/1971 | Svokos et al. | 260/243 R |
| 3,637,684 | 1/1972 | Goldman | 260/243 R |
| 3,879,398 | 4/1975 | Ellerton et al. | 260/243 C |
| 3,936,447 | 2/1976 | Peterson et al. | 260/243 C |

FOREIGN PATENT DOCUMENTS

| 1,034,573 | 6/1964 | United Kingdom | 260/243 R |

Primary Examiner—Donald G. Daus
Assistant Examiner—David E. Wheeler
Attorney, Agent, or Firm—Weiser, Stapler & Spivak

[57] ABSTRACT

An improved process for preparing 4-thia-2,6-diazabicyclo[3,2,0]hept-2-ene-7-ones such as methyl 3-phenoxy-4-thia-2,6-diazabicyclo[3,2,0]hept-2-ene-7-one-6-isopropenylacetate which comprises extruding sulfur from dithiazeneazetidinones such as methyl 3-phenoxymethyl-4,5-dithia-2,7-diazabicyclo[4,2,0]-oct-2-ene-8-one-7-isopropenylacetate. The compounds obtained are useful intermediates in the preparation of certain 3-cephems.

12 Claims, No Drawings

THIAZOLENEAZETIDINONES FROM DITHIAZENEAZETIDINONES

PRIOR ART

There is disclosed in the prior art certain thiazoleneazetidinones 1 of the formula:

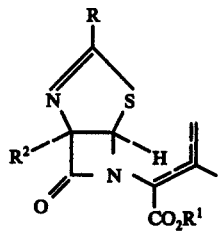

wherein R stands for benzyl or phenoxymethyl, $R^2$ stands for hydrogen and $R^1$ is a cleavable radical. The compounds since they are obtained from natural penicillin G or V can thus only yield corresponding cephems in any synthetic routes. These compounds thus provide a limited utility in the synthesis of cephalosporins and penicillins.

THE INVENTION

In accordance with the present invention there is provided a novel process for preparing thiazoleneazetidinones 1 of the general formula:

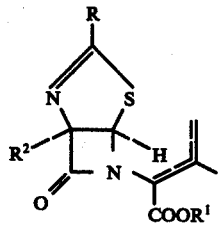

wherein:
R stands for phenoxyloweralkyl, phenylthioloweralkyl, benzyl, lower alkyl, phenyl, heteroaryl, heteroarylmethyl, α-aminobenzyl and protected derivatives thereof, 4-amino-4-carboxy-1-butyl and protected derivatives thereof, $R^3O-$, $R^3S-$, and $R^3R^4N-$ where $R^3$ is lower alkyl, phenyl, heteroaryl, or arylloweralkyl. $R^4$ is hydrogen or radical $R^3$,
$R^2$ is hydrogen or methoxy;
$R^1$ is hydrogen, lower alkyl, loweralkoxymethyl, aryloxymethyl, 2,2,2-trichloroethyl, benzyl, p-nitrobenzyl, benzhydryl, phenacyl, or trimethylsilyl.

Formula 1 is representative of the two isomers depicted by 1a and 1b.

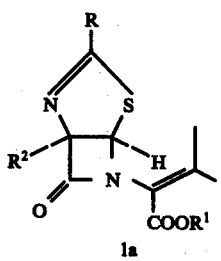

1a

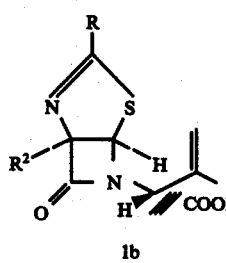

1b

The novel process of the present invention comprises extruding sulfur from dithiazeneazetidinones 2 of the formula:

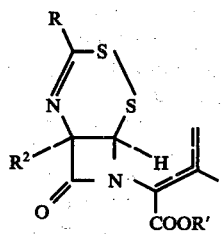

wherein R, $R^1$ and $R^2$ are as defined previously.

The extrusion of sulfur from the dithiazeneazetidinones 2 may be carried out in a number of ways. In accordance with the present invention it is understood that the expression "extrusion of sulfur" comprises any procedure which will effectively remove one sulfur atom from a dithiazeneazetidinone 2. Such procedures include photolysis or heating or the use of "sulfur abstraction compounds" such as trivalent phosphorus compounds or the use of compounds such as pyridinium dichloromethylphosphonate, Lewis acids, aqueous strong acids, iodine and sulfenyl iodides. For example sulfur can be extruded by photolysis or heating alone in a suitable solvent for a period of time which depends on the compound 2 used. The solvent may be an organic inert solvent such as dioxane. The abstraction of sulfur may also be carried out in the presence of water or a catalyst such as pyridinium dichloromethylphosphonate or a sulfur abstraction compound such as triphenyl phosphine, trimethyl phosphite or tris(dimethylamine)-phosphite. Also extrusion of sulfur from the dithiazeneazetidinones 2 to the desired thiazoleneazetidinones can be carried out by treatment with iodine, sulfenyl iodides such as benzothiazole-2-sulfenyl iodide or with metal salts (Lewis acids) such as for example antimony pentachloride or tin chloride, in an inert solvent such as for example toluene, methylene chloride or dioxane; and aqueous strong acids such as for example methane sulfonic acid.

The choice of the sulfur extrusion process will depend on the value of the substituent R. For example when R stands for phenoxy ($\phi O-$) or phenoxymethyl ($\phi OCH_2$) the prefered reagent for the conversion of 2 to 1a is iodine or sulfenyl iodides such as benzothiazole-2-sulfenyl iodide, followed by treatment with sodium thiosulfate.

The starting dithiazeneazetidinones 2 are conveniently obtained from penicillin sulfoxide thioamides 3 of the general formula:

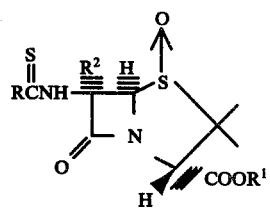

The dithiazeneazetidinones 2 may also be obtained by the method described in copending application Ser. No. 589,560 filed June 23, 1975, now abandoned incorporated herein by reference. In application Ser. No. 589,560 the term "protected derivative", as it relates to alpha-aminobenzyl, is defined as follows: alpha-aminobenzyl and protected derivatives such as the carbamates (benzyl, trichloroethyl and methoxymethyl).

The thiazoleneazetidinones 1, are particularly useful intermediates in the preparation of cephalosporins and penicillins. For example, the thiazoleneazetidinones 1 react with sulfenyl chlorides to form unsym-azetidinone disulfides, 3 (W. G. E. Underwood, Glaxo Labs Ltd., Ger. Offen. No. 2,303,889, 26 Jan. 1973), which upon reaction with iodine will form the 3-iodocephams; 4, as disclosed in copending appl. Ser. No. 589,561, filed June 23, 1975, incorporated herein by reference, which upon dehydroiodination will provide the corresponding 3-cephems, 5. Also the thiazoleneazetidinones 1, react with iodine or better sulfenyl iodides in presence of moisture, to form the 3-iodocephams, 4 which are readily dehydroiodinated to the 3-cephems, 5 (see Flowsheet 1 below).

FLOWSHEET 1

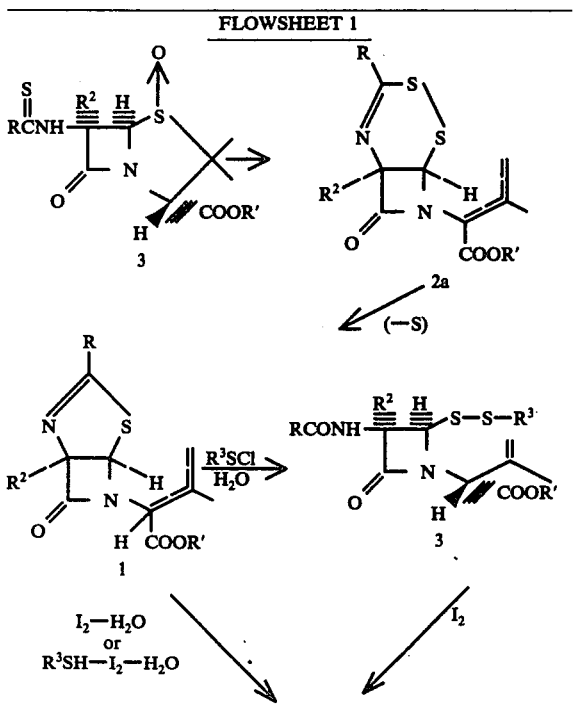

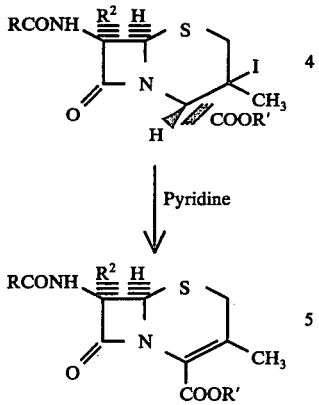

Also within the scope of the present invention are those compounds where R stands for $R^3O-$, $R^3S-$, and $R^3R^4N-$ wherein $R^3$ and $R^4$ are as previously defined. The advantage of the new compounds where R stands for $R^3O-$, $R^3S-$, and $R^3R^4N-$ over the known compounds where R stands for benzyl ($\phi CH_2-$) or phenoxymethyl ($\phi OCH_2-$) is that they are better suited to certain chemical reactions usually employed in the chemical modification of these compounds. Thus brominations employing N-bromosuccinimide would be expected to give a cleaner product with those compounds derived from 1 ($R = R^3O-$, $R^3S-$, and $R^3R^4N-$ with $R^3$ being phenyl and heteroaryl) while with compounds 1 ($R = \phi CH_2$, and $\phi OCH_2$) bromination of the methylene group would be an added complication.

The starting penicillin sulfoxide thioamides 3 are themselves obtained in a number of ways. The penicillin sulfoxide thioamides 3 where R stands for $R^3O-$, $R^3S-$, and $R^3R^4N-$, and $R^2$ stands for H may be conveniently obtained by thioacylation of 6-aminopenicillanic acid sulfoxide with a thioacylating agent corresponding to the following formulae: $RCSCl$, $RCSYR^3$, $CS_2/R^3X$, $R^3N=C=S$, $CSCl_2/R^3R^4NH$, wherein $R^3$ and $R^4$ are as previously defined, Y is sulfur or oxygen and X is halogen. The thioacylation reaction is carried out in the manner known in the art. This procedure is illustrated in Flowsheet 2. It is also possible to obtain the penicillin sulfoxide thioamides 3 wherein R stands for $R^3O-$, $R^3S-$ or $R^3R^4N-$ by treating a 6-isothiocyanate of penicillanic acid sulfoxide with an alcohol of the formula $R^3OH$, a thiol of the formula $R^3SH$, or a secondary amine of the formula $R^3R^4NH$.

FLOWSHEET 2

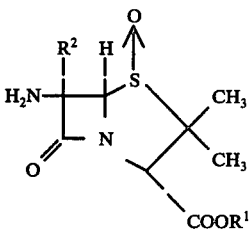

FLOWSHEET 2

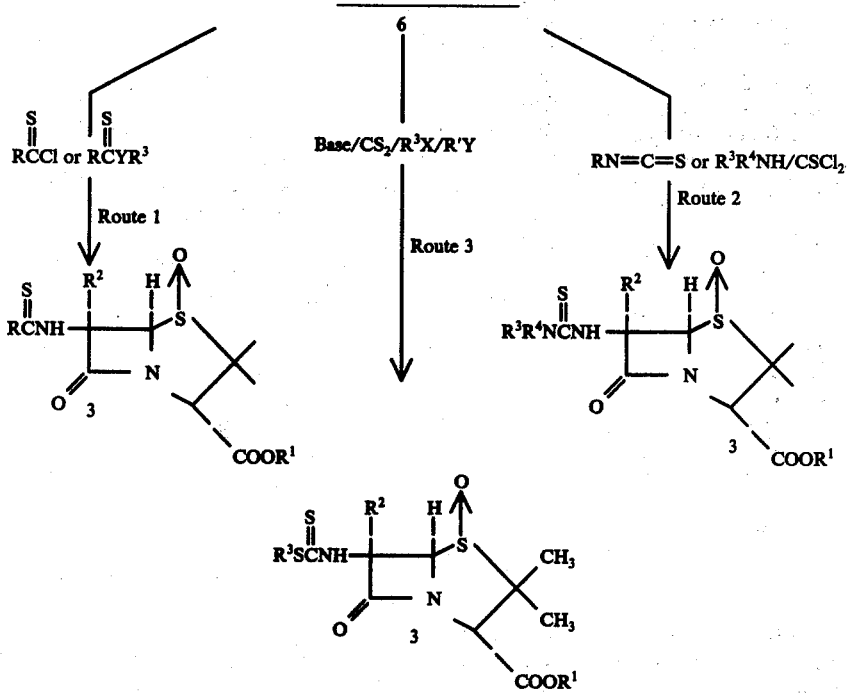

Alternatively, the penicillin sulfoxide thioamides 3, may be derived from Penicillin G, N or V sulfoxides in which case R is benzyl when starting from penicillin G, R is phenoxymethyl when starting from Penicillin V and R is 4-amino-4-carboxy-1-butyl when starting from Penicillin N, in which case it is preferred to protect the amino group by acylation and the carboxy group by esterification. The precipitation of the penicillin sulfoxide thioamides 3 may be schematically illustrated by reference to Flowsheet 3.

FLOWSHEET 3

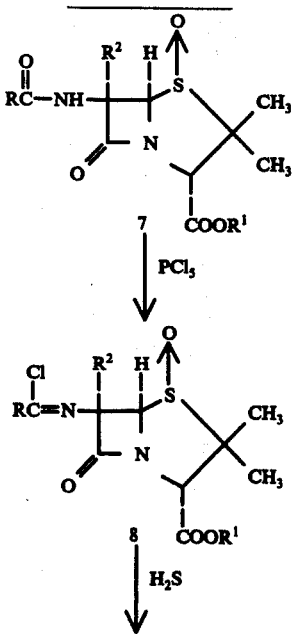

-continued
FLOWSHEET 3

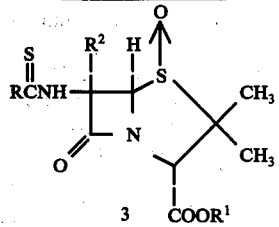

More particularly, Penicillin G sulfoxide, Penicillin N sulfoxide or Penicillin V sulfoxide 7 is chlorinated with a suitable agent such as phosphorus pentachloride in the presence of a base such as dimethylaniline or pyridine. Other procedures for the preparation of haloimines, 8, may also be used. The chloroimine compound 8 is then readily transformed to its corresponding thioamide 3 by reaction with hydrogen sulfide in the presence of an acid catalyst such as hydrogen chloride or sulfuric acid or the like.

It should be appreciated that the thiazoleneazetidinones 1 of the present invention are useful intermediates for the preparation of cephalosporins. For example, on treatment with sulfenyl iodides they provide 3-iodocephams which can be converted to the cephem compounds, such as 7-ADCA (7-aminodesacetoxycephalosporinic acid) by methods known to the art.

EXAMPLES

The present invention will be more readily understood by referring to the following Examples which are given only to illustrate the invention rather than limit its scope.

EXAMPLE 1

METHYL 6-PHENOXYTHIOACETAMIDOPENICILLANATE SULFOXIDE (R = $\phi OCH_2$—, $R^1$ = $CH_3$)

Phosphorus pentachloride (26.4 g., 0.126 moles) was added in one lot to a stirred, cold (−70°) solution of methyl penicillin V sulfoxide (45.0 g., 0.1185 mole) and dimethylaniline (36.3 g., 0.3 moles) in methylene chloride (600 ml). and the mixture stirred for 2½ hrs. at −50° or lower. $H_2S$ is then bubbled into the reaction mixture at −70° and after approximately ¼ hr. the mixture becomes a clear yellow from a clear dark brown colour. The $H_2S$ is continued for 1 hr. at −50° and the mixture warmed to 0° by applying an ice bath. The $H_2S$ addition is continued at 0° C. for 1½ hrs, after which the reaction mixture is poured into ice water (750 ml) and the resulting mixture stirred with aqueous sodium bicarbonate (90 g. in 200 ml). The layers were separated and the organic layer extracted sequentially with water (300 ml), aqueous HCl (3 molar, 2 × 300 ml) and salt water (300 ml). The organic layer was dried ($MgSO_4$), filtered and the filtrate concentrated to a yellow powder, 44.5 g., which was estimated to contain about 60% of methyl 6-phenoxythioacetamidopenicillanate sulfoxide from its nmr spectrum.

The crude thioamide was purified by column chromatography over silica gel (Grace Davidson SMR7-1498 grade 951-MS, 450 g.) using chloroform as eluent and collecting about 50 ml fractions. The process was monitored by tlc of the fractions. Fractions 11 to 145 contained the thioamide and were combined and concentrated to give 26.6 g. of the thioamide which was washed with methanol to give 22.8 g. of pure thioamide. An analytical sample was obtained by recrystallization from methanol as white crystals, m.p. 144°–145°.

Analysis: Calcd. C, 51.51; H, 5.05; N, 7.07; S, 16.16. Found C, 51.55; H, 5.03; N, 7.08; S, 15.83.

The ir and nmr spectra were in agreement with the assigned structure. The nmr spectrum was quite characteristic and differed appreciably from the starting amide. The nmr ($CDCl_3$) spectrum had signals at δ1.23(s,3H), 1.73(s,3H), gem. $CH_3$; 3.85(s,3H), $COOCH_3$; 4.73(s,1H), $C_3$-H; 4.95(s,2H), —$OCH_2$—; 5.20(d,1H,J=5cps), $C_5$-H; 6.67 to 7.40 m,6H), $C_6H_5$ and $C_6$—H; 9.78(d,1H), —CSNH—.

The methyl penicillin V sulfoxide was collected in later fractions.

EXAMPLE 2

6-PHENOXYTHIOACETAMIDOPENICILLANIC ACID SULFOXIDE 3 (R = $\phi OCH_2$—, $R^1$ = H)

Anhydrous penicillin V sulfoxide (1.098 g., 3 mmoles, prepared by drying penicillin V sulfoxide at 60° C. under vacuum over $P_2O_5$ to constant weight) and dimethylaniline (1.14 ml., 9 mmoles) were dissolved in dry methylene chloride (20 ml., dried by distillation over $P_2O_5$) and cooled to 0° C. Trimethylchlorosilane (0.418 ml., 3.3 mmoles) was added and the yellow solution stirred for 30 mins at 0° C. The mixture was then cooled to −30° and $PCl_5$ (0.685 g., 3.3 mmoles) added. The mixture was stirred for 3 hours at −35° to −25°, by which time the mixture became a dark green colour. $H_2S$ was then passed through the stirred solution. On contact with $H_2S$, the green colour was immediately discharged. After 30 mins the temperature of the reaction mixture was raised to 0° by placing it in an ice-bath and, after stirring a further 30 mins at this temperature, the $H_2S$ addition was discontinued and nitrogen was passed through the mixture which was diluted with methylene chloride. The mixture was extracted with saturated aqueous sodium bicarbonate (3 times, until the pH of the aqueous layer was 8). The alkaline solution was then extracted with ether (4 times) and then acidified to pH 2.0 with hydrochloric acid (3 normal). At this stage some of the compound precipitated. The mixture was extracted with ethyl acetate (3 times). The combined organic extracts were washed with water, dried over $Na_2SO_4$ and taken to dryness to give 0.73 g. of a yellow solid, whose thin layer chromatogram and ir and nmr spectra showed a mixture of the amide and thioamide. The 6-phenoxythioacetamidopenicillanic acid sulfoxide was estimated to be present in about 70% yield from the nmr spectrum. Purification of this thioamide can be effected by column chromatography, using silicic acid.

EXAMPLE 3

6-PHENOXYTHIOCARBAMIDOPENICILLANIC ACID SULFOXIDE 3 (R = $\phi O$—, $R^1$ = H)

Aqueous potassium hydroxide (2 normal) was added slowly to an ice-cold stirred suspension of 6-APA sulfoxide (23.2 g., 0.1 mole) in water (275 ml), until a pH of 8.0. The solution was diluted with THF (125 ml). The solution was stirred in the ice-bath and separate solutions of phenoxythiocarbamoyl chloride (17.2 g., 0.1 mole) in THF (50 ml.) and aqueous KOH (2 normal) added by two separate dropping funnels at such a rate as to maintain the pH constant at 8.0. The reaction mixture was stored in a refrigerator overnight and then extracted with ethyl acetate (2 × 250 ml.). The water layer was covered with ethyl acetate (150 ml.) in an ice-bath and the pH adjusted to 1.5 with hydrochloric acid (12 normal). The layers were separated and the aqueous layer extracted with ethyl acetate (2 × 125 ml). The combined ethyl acetate layers were dried over $MgSO_4$, concentrated and dried under vacuum to yield 34.3 g. (92%) of the crude 6-phenoxythiocarbamidopenicillanic acid sulfoxide as a yellow brown foam.

The product was further purified by stirring with ether (3 × 25 ml per gram of crude), filtering and discarding the insoluble yellow solid. The ether filtrate was treated with decolorizing charcoal, filtered and concentrated to a small volume. The white solid that separated (about 50% recovery) had m.p. 153° – 156° (decomp), and nmr and ir spectra in agreement with the proposed structure.

Analysis: Calcd. C, 48.91; H, 4.34; N, 7.60; S, 17.39. Found C, 48.63; H, 4.68; N, 7.41; S 17.30.

EXAMPLE 4

METHOXYMETHYL 6-PHENOXYTHIOCARBAMIDOPENICILLANATE SULFOXIDE 3 (R = $\phi O$, $R^1$ = $CH_3OCH_2$—)

Chloromethylmethyl ether (2.66 g., 0.033 mole) was added slowly to an ice-cold stirred solution of 6-APA sulfoxide (6.96 g., 0.03 mole) and triethylamine (6.66 g., 0.066 mole) in methylene chloride (50 ml) and the reaction mixture stirred in the ice-bath for ½ hr. Phenoxythiocarbonyl chloride (5.7 g., 0.033 mole) was then added slowly, when a mild exothermic reaction (the temp rising to 5°) occurred. The reaction mixture was stirred an additional hour, by which time the yellow solution containing a moderate amount of solid had become almost clear and black. The reaction mixture was washed with water (2 × 30 ml.), dried (MgSO$_4$ with added decolorizing carbon) filtered and concentrated to 11 g. (88.7%) of a brown foam. The solid was stirred with ethyl acetate (200 ml) for ½ hr and filtered and the solid washed with ethyl acetate. The combined filtrates on concentration gave 8.4 g. (67.7%) of methoxymethyl 6-phenoxythiocarbamidopenicillanate sulfoxide as a yellow foam whose ir and nmr spectra were in agreement with the assigned structure.

EXAMPLE 5

METHYL 6-METHYLDITHIOCARBAMIDOPENICILLANATE SULFOXIDE 3 (R = CH$_3$S and R$^1$ = CH$_3$) and 6-METHYLDITHIOCARBAMIDOPENICILLANIC ACID SULFOXIDE 3 (R = CH$_3$S, R$^1$ = H)

Carbon disulfide (3.35 g., 0.044 mole) was added to an ice-cold stirred solution of 6-APA sulfoxide (9.28 g., 0.04 mole), and triethylamine (8.5 g., 0.084 mole) in dry DMF (25 ml). After ½ hour stirring in the ice-bath, methyl iodide (12.4 g., 0.088 mole) was added, the mixture stirred an additional hour in the ice-bath and then stirred at ambient temperature overnight (16 hours). The solution was poured, with vigorous stirring into excess water when a sticky solid separated. The solid was taken up in chloroform, the organic layer washed with water (3 × 50 ml); dried over MgSO$_4$ with decolorizing carbon, filtered, and the filtrate concentrated to a brown foam 8.6 g., (62%). The nmr and ir spectra indicated that the desired compounds were present in the product. A tlc using ether as the developing solvent and iodine for visualizing the components, indicated the presence of at least four components.

The crude product (5.0 g.) was purified by chromatography on silicic acid (250 g.) using ether as eluant and collecting fractions (10 ml.). White crystals appeared in many of the fractions 48 - 82, which all showed the same component to be present by tlc. These crystals, from the nmr spectrum were a mixture of the methyl 6-methyldithiocarbamidopenicillanate sulfoxide (II) and 6-methyldithiocarbamidopenicillanic acid sulfoxide (II) in a ratio of about 2:1. These fractions were combined and concentrated to give 2.7 g. of a brown foam whose nmr spectrum indicated a mixture of the methyl ester and the acid in the ratio of about 1:1. A partial separation could be effected with ether.

The methyl ester was obtained pure by treating a solution of the mixture in chloroform with aqueous sodium bicarbonate, drying the organic layer and concentrating, whereby the methyl ester was obtained as a white foam, m.p. 138° - 142°. The ir and nmr spectra were in agreement with the assigned structure and the C,H values were within 0.4% of the calculated values.

Analysis: Calcd. C, 39.28; H, 4.76. Found. C, 39.06; H, 5.09.

A high resolution mass spectral analysis of this compound gave a mass of 336.0268 for the parent ion. Calculated for C$_{11}$H$_{16}$N$_2$S$_3$$^{32}$O$_4$ is 336.0273.

An attempt to recover the acid from the bicarbonate layer was not successful.

EXAMPLE 6

METHOXYMETHYL 6-METHOXYMETHYLDITHIOCARBAMIDOPENICILLANATE SULFOXIDE 3 (R = CH$_3$OCH$_2$S and R$^1$ = CH$_3$OCH$_2$—)

Carbon disulfide (1.7 g., 0.022 moles) was added to an ice-cold, stirred solution of 6-APA sulfoxide (4.65 g., 0.02 mole) and triethylamine (4.9 g., 0.048 mole) in methylene chloride (65 ml), and the mixture stirred ½ hour in the ice-bath and 1 hour at room temperature. The mixture was cooled in an ice-bath and chloromethylmethyl ether (3.5 g., 0.044 mole) added dropwise over ½ hour. The reaction mixture was stirred an additional hour in the ice-bath, then at room temperature for 1 hour, finally cooled and washed rapidly with ice-water (3 × 20 ml). The organic layer was dried (MgSO$_4$) and concentrated to 6.1 g. of the methoxymethyl 6-methoxymethyldithiocarbamidopenicillanate sulfoxide as a sticky yellow solid. The ir and nmr spectrum of this compound were in agreement witht the assigned structure. The compound underwent rapid hydrolysis with water and became quite sticky on exposure to the air.

EXAMPLE 7

METHOXYMETHYL 6-METHYLDITHIOCARBAMIDOPENICILLANATE SULFOXIDE 3 (R = CH$_3$S, R$^1$ = CH$_3$OCH$_2$—)

Chloromethylmethyl ether (2.5 g., 0.03 mole) was added to an ice-cold, stirred solution of 6-APA sulfoxide (6.9 g., 0.03 mole), and triethylamine (9.1 g., 0.09 mole) in methylene chloride, and the reaction mixture stirred for an additional ½ hour in the ice-bath. A mixture of carbon disulfide (2.4 g., 0.03 mole) and methyl iodide (8.6 g., 0.06 mole) in methylene chloride (20 ml.) was added slowly to the cold (10° C) stirred reaction mixture, which was then stirred an additional 2 hours at ambient temperature. The mixture was stirred with water. (It was necessary to add an excess of ethyl acetate to break the emulsion). The separated organic layer was washed with water (2 times), dried over MgSO$_4$ with decolorizing carbon, filtered through celite, and the filtrate concentrated to a light yellow foam weighing 3.7 g. (34%) which was the methoxymethyl 6-methyldithiocarbamidopenicillanate sulfoxide.

EXAMPLE 8

TRIETHYLAMMONIUM 6-METHYLAMINOTHIOCARBAMIDOPENICILLANATE SULFOXIDE 3 (R = CH$_3$NH, R$^1$ = (C$_2$H$_5$)$_3$NH)

Methylisothiocyanate (4.1 g., 0.055 mole) was added to an ice-cold, stirred solution of 6-APA sulfoxide (11.6 g., 0.05 mole), and triethylamine (11.1 g., 0.11 mole) in methylene chloride. The reaction mixture was stirred an additional hour in the ice-bath, then for 2 hours at ambient temperature, then treated with decolorizing charcoal, filtered through celite and taken to dryness. The resulting yellow foam was triturated with ether, filtered, washed with ether and dried at the pump to provide 19.7 g. (97%) of a flesh-colored powder which was the triethylammonium 6-methylaminothiocarbamidopenicillanate sulfoxide. The ir and nmr spectra of the product were in agreement with the assigned structure.

The triethylammonium salts were converted to esters, such as the methyl esters, before the thermolysis to the 1,2,4-dithiaaz-3-enes. It is also possible to convert them to the trimethylsilyl esters prior to thermolysis.

EXAMPLE 9
TRIETHYLAMMONIUM 6-PHENYLAMINOTHIOCARBAMIDOPENICILLANATE SULFOXIDE 3 (R = φNH, R¹ = (C₂H₅)₃NH)

Triethylammonium 6-phenylaminothiocarbamidopenicillanate sulfoxide was made in the same way as in Example 8, by the action of phenylisothiocyanate on 6-APA sulfoxide in the presence of triethylamine. The compound was obtained as a pale yellow powder, m.p. 145° - 148° (decomp) in 100% yield. The ir and nmr spectra were in agreement with the assigned structure.

The triethylammonium salts were converted to esters, such as the methyl esters, before the thermolysis reactions. It is also possible to convert them to the trimethylsilyl esters prior to thermolysis.

EXAMPLE 10
METHYL 6-PHENOXYTHIOAMIDOPENICILLANATE SULFOXIDE, 3 (R = φO, R' = CH₃, R² = H)

A solution of 6-phenoxythioamidopenicillanic acid sulfoxide in tetrahydrofuran was stirred in an ice-bath and a solution of diazomethane (1.2 equivalents) in ether added. After stirring in the ice bath an additional 15 minutes, the resulting solution was treated with charcoal, filtered and concentrated to dryness when a yellow foam resulted. A very small volume of methanol was added, when the foam dissolved readily. After a short time the methyl ester began to crystallise as pale yellow crystals. The mixture was stirred in an ice bath and the resulting crystals isolated in over 80% yield by filtration. The recrystallised material, m.p. 148° - 150° on mass spectral analysis gave a measured m/e of 382.0665, while that calculated for $C_{16}H_{18}N_2O_5S_2^{32}$ is 382.0658. The ir and nmr spectra were consistent for the assigned structure. The nmr spectrum (CDCl₃) δ8.32 (d, 1H, NH), 7.59 to 7.05 (m, 5H, C₆H₅), 6.50 (q, 1H, C₆—H), 5.23 (d, 1H, C₅—H), 4.77 (s, 1H, C₃—H), 3.82 (s, 3H, COOCH₃), 1.70 and 1.25 (ss, 6H, gem- CH₃) is characteristic of this compound.

EXAMPLE 11
METHYL 3-PHENOXYMETHYL-4,5-DITHIA-2,7-DIAZABICYCLO(4,2,0)OCT-2-ENE-8-ONE-7-ISOPROPENYLACETATE, 2 (R = φOCH₂, R² = H), from METHYL PENICILLIN V THIOMIDE SULFOXIDE, 3 (R = φOCH₂, R' = CH₃, R² = H)

A solution of pure methyl 6-phenoxythioacetamidopenicillanate sulfoxide (500 mg., 1.3 mmoles) in toluene (125 ml) was heated (in an oil bath at 120° C) with stirring under reflux, under nitrogen, in a flask fitted with a Dean-Stark trap for 2 to 3½ hrs. The toluene was removed in vacuo. An nmr spectrum (CDCl₃) of the waxy residue showed complete reaction and formation of methyl 3-phenoxymethyl-4,5-dithia-2,7-diazabicyclo-(4,2,0)oct-2-ene-8-one-7-isopropenylacetate, 2 (R = φOCH₂, R' = CH₃, R² = H), δ7.5 to 6.9 (m, 5H, C₆H₅), 5.72 (d, with wings, 2H, β-lactam protons), 5.19 and 5.09

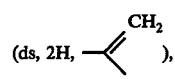
(ds, 2H, 4.95 (s, 1H, CHCOOCH₃), 4.87 (s, 2H, —OCH₂—), 3.8 (s, 3H, COOCH₃), 1.90

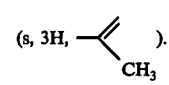
(s, 3H,

There was no trace of the α,β double bond isomer in the nmr spectrum.

Exactly the same results are obtained by using purified dioxane in place of toluene as solvent. In this case, instead of the Dean-Stark trap, the reaction flask was fitted with a Soxhlet extractor, whose thimble is packed with a drying agent such as magnesium sulfate.

In certain cases, particularly with old samples of the thioamide, 3, thermolysis under the conditions described above gave a mixture of products. It was found that the addition of dimethylaniline (preferably about ½ mole equivalent per mole of thioamide) before thermolysis gave a reproducible quantitative yield of the dithiazeneazetidinone, 2, on thermolysis. The dimethylaniline could be removed from the reaction product (in a toluene, methylene chloride, or chloroform solution) by rapid washing with aqueous dilute hydrochloric acid (0.5 normal).

EXAMPLE 12
METHYL 3-PHENOXYMETHYL-4,5-DITHIA-2,7-DIAZABICYCLO(4,2,0)OCT-2-ENE-8-ONE-7-PROPENYLACETATE, 2 (R = φOCH₂, R¹ = CH₃, R² = H) BY ISOMERISATION

The βγ double bond isomer, (200 mg., 0.505 mmoles) was made by the method described in Example 11. The toluene used as solvent was removed and immediately replaced and purified tetrahydrofuran, the resulting solution being cooled to −60° C. Dimethylamine (23 mg., 0.505 mmoles) was added and the reaction mixture kept at −60° C for ½ hour and then concentrated in vacuo. The resulting product was the αβisomer, as shown by the nmr spectrum (CDCl₃): δ7.47 to 6.82 (m, 5H, C₆H₅), 5.77 and 5.62 (ABq, J=5Hz, 2H, β-lactam protons), 4.84 (d, J=1Hz, 2H, —O—CH₂—), 3.77 (s, 3H, COOCH₃), 2.24 and 2.02 (ss, 6H, =C(CH₃)₂).

EXAMPLE 13
METHYL 3-PHENOXYMETHYL-4-THIA-2,6-DIAZABICYCLO(3,2,0)HEPT-2-ENE-7-ONE-6-ISOPROPENYLACETATE, 1b (R = φOCH₂, R¹ = CH₃, R² = H) by THERMOLYSIS OF METHYL PENICILLIN V THIOAMIDE SULFOXIDE 3, VIA 2

A solution of methyl penicillin V thioamide sulfoxide (0.5 g., 1.26 mmoles) and bis-(trimethylsilyl)trifluoroacetamide (0.36 g., 1.40 mmoles) in purified dioxane (250 ml) was heated under reflux (in an oil bath at 120° C) in an Argon atmosphere using a Soxhlet apparatus for the removal of moisture (the Soxhlet thimble being packed with magnesium sulfate). The course of the reaction was followed by removing aliquots of the reaction mixture, concentrating to dryness and obtaining nmr spectra. Estimations could be made by utilising the characteristic signals of certain groups in the compounds. Thus, the gem. dimethyl signals of the penicillin sulfoxide at ca. δ1.22 and 1.75, the 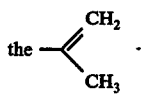

signal at ca. δ1.9 and the characteristic β-lactam signals at δ5.72 characterised 2, while 1b was identified by its

singlet at δ1.75 and its β-lactam signals at δ6.0, among others. The following results were obtained:

| Time of Heating | Estimated Percentage | | |
|---|---|---|---|
| | Compound 3 | Compound 2b | Compound 1b |
| 1 hr | 50% | 50% | — |
| 2 hr | 38% | 62% | — |
| 3 hr | 14% | 80% | — |
| 23 hr | — | 65% | 35% |
| 30 hr | — | 50% | 50% |
| 48 hr | — | 10% | 90% |

It should be noted that throughout this thermolysis there was no indication in the nmr spectra of any formation of the αβ isomers 1a or 2a. Other experiments without added silylating agents have shown that after 3½ to 4 hrs the conversion of 3 to 2 is virtually complete, and no detectable amounts of 1 are present, and with extended reaction times compound 1b is formed. This reaction is dependent on the purity of the solvent.

EXAMPLE 14

METHYL 3-PHENOXYMETHYL-4-THIA-2,6-DIAZABICYCLO(3,2,0)HEPT-2-ENE-7-ONE-6-ISOPROPENYLACETATE, 1b, BY THE ACTION OF IODINE AND SODIUM THIOSULFATE ON 2b

Methyl 3-phenoxymethyl-4,5-dithia-2,7-diazabicyclo-(4,2,0)oct-2-ene-8-one-7-isopropenylacetate, 2b, reacted immediately with iodine (1 atomic equivalent or 1 molar equivalent) in organic solvents such as toluene or dioxane to give different adducts (depending on the ratio) as was evident from the nmr spectra of the residues. When these adducts in an organic solvent such as toluene or methylene chloride were stirred with aqueous thiosulfates, they were converted in near quantitative yields to compound 1b, which was isolated by drying the organic layer over magnesium sulfate, filtering and concentrating. Identity of the product was established by direct comparison (ir and nmr spectra) with an authentic sample of 1b.

EXAMPLE 15

3-PHENOXY-4,5-DITHIA-2,7-DIAZABICYCLO(4,2,0)OCT-2-ENE-8-ONE-7-ISOPROPENYLACETIC ACID, 2b (R = φO, R¹ = H, R² = H)

A solution of 6-phenoxythiocarbamidopenicillanic acid sulfoxide, 3 (R = φO, R¹ = H, R² = H) (15 g., 0.04 mole) in purified dioxane (300 ml) was heated with stirring under reflux in a dry nitrogen atmosphere in an oil bath maintained at 130° C, for 4 hrs. The reaction mixture was concentrated in vacuo and dried under hivac. The yellowish brown solid thus obtained was dissolved in the minimum amount of warm acetone, the solution treated with charcoal and filtered. The filtrate was concentrated to about ⅓ its volume and just sufficient hexane added to induce crystallization. The mixture was cooled overnight at about −10° C and the resulting pale yellow crystals isolated by filtration and drying, when 10.5 g (75%) of 3-phenoxy-4,5-dithia-2,7-diazabicyclo(4,2,0) oct-2-ene-8-one-7-isopropenylacetic acid was obtained. The compound could be purified by recrystallization from acetone-hexane. It was obtained as white crystals, m.p. 146°-148° dec. A high resolution mass spectral analysis gave a mass of 350.0404 for the parent ion, that calculated for $C_{15}H_{14}N_2S_2^{32}O_4$ being 350.0396. The nmr (DMSOd₆) spectrum δ7.68 − 7.15 (m, 6H, $C_6H_5$ and COOH), 5.87 and 5.53 (ABq, 2H, J = 5Hz, β-lactam protons cis-fused), 5.2

(s, 2H, 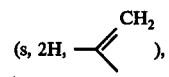), 4.85 (s, 1H, —CHCOOH), 1.89

(s, 3H, 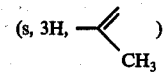)

is in agreement with the assignment.

EXAMPLE 16

METHYL 3-PHENOXY-4,5-DITHIA-2,7-DIAZABICYCLO(4,2,0)OCT-2-ENE-8-ONE-7-ISOPROPENYL ACETATE, 2b (R = φO, R¹ = CH₃, R² = H)

3-Phenoxy-4,5-dithia-2,7-diazabicyclo(4,2,0)oct-2-ene-8-one-7-isopropenylacetic acid (10.0 g., 28.5 mmole) was dissolved in tetrahydrofuran (250 ml) and the solution cooled in an ice-bath. Excess of diazomethane in ether (100 ml) was added and the solution stirred in the ice-bath for 0.5 hr and then concentrated in vacuo. The residue was taken up in the minimum of ether and cooled in a dry ice-acetone bath while adding an equal volume of hexane. The resulting white precipitate was filtered off and dried to give 7.0 g of the product. A further 1.5 g., was obtained from the mother liquor after concentration and repeating the ether-hexane precipitation. The two crops were combined (8.5 g., 81%) since they were identical (nmr spectra and tlc). The nmr (CDCl₃) spectrum: δ7.6 to 7.1 (m, 5H, C₆H₅), 5.7 and 5.48 (ABq, 2H, J = 4Hz, β-lactam protons cis-fused), 5.22 and 5.12

(d, s, 2H, 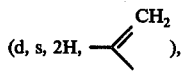), 5.0 (s, 1H, CHCOOCH₃), 3.8 (s, 3H, COOCH₃), and 1.97

(s, 3H, 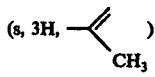)

is in agreement with the assigned structure.

The same compound was also obtained by thermolysing methyl 6-phenoxythioamidopenicillanate sulfoxide in toluene or dioxane as solvent for about 4 hrs.

EXAMPLE 17
METHYL 3-PHENOXY-4-THIA-2,6-DIAZABICYCLO(3,2,0)HEPT-2-ENE-7-ONE-6-ISOPROPENYLACETATE, 1b (R = φO, R¹ = CH₃, R² = H) FROM THE REACTION OF 2b WITH IODINE

A solution of methyl 3-phenoxy-4,5-dithia-2,7-diazabicyclo(4,2,0)oct-2-ene-8-one-7-isopropenylacetate, 2b, (2 g., 0.005 moles) in methylene chloride (50 ml) was stirred with iodine (1.4 g., 0.005 moles) at ambient temperature for 12 hrs [Note: nmr spectra run on a similar reaction showed that this reaction was comparatively slow and did not (unlike the reaction with 2b (R = φOCH₂) in Example 14) require sodium thiosulfate for the formation of 1b. The sodium thiosulfate was used in this reaction only to remove the iodine]. The reaction mixture was washed with aqueous sodium thiosulfate (2 × 50 ml), then water (2 × 50 ml), dried over magnesium sulfate, filtered and concentrated to give 1.9 g., of a yellow foam. The nmr spectrum (CDCl₃) of this foam showed the presence of 2a (78%), mixed with the 3-iodocepham (22%-characterised by the C₃—CH₃ singlet at ca. δ2.2 and the C₂—CH₂ quartet at δ3.0). The compound was purified by column chromatography on Mallinckrodt SilicAr CC-7, using hexane:ether (1:1) as the eluant. The material crystallised from ether-hexane as floculant silky white needles, m.p. 110° - 112°. The nmr spectrum (CDCl₃) δ7.38 (br s, 5H, C₆H₅), 6.12 and 5.72 (ABq, J = 4Hz, 2H, β-lactam protons cis-stereochemistry), 5.22 and 5.08

(br s, s, 2H—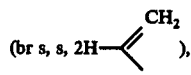), 4.99 (s, 1H, CHCOOCH₃), 3.85 (s, 3H, COOCH₃), 1.95

(s, 3H, —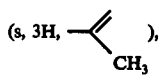), and mass spectrum — Calc'd for C₁₆H₁₆N₂S³²O₄, 332.0831; measured 332.0826 with a strong peak corresponding with M + 1, are in accordance with the assigned structure.

EXAMPLE 18
METHYL 3-PHENOXY-4-THIA-2,6-DIAZABICYCLO(3,2,0)HEPT-2-ENE-7-ONE-6-ISOPROPENYLACETATE, 1b (R = φO, R¹ = CH₃, R² = H) FROM THE REACTION OF 2b with TIN(II)CHLORIDE Hydrated stannous chloride (0.27 g., 6.86 × 10⁻⁴ mole) was added to a solution of methyl 3-phenoxy-4,5-dithia-2,7-diazabicyclo(4,2,0)oct-2-ene-8-one-7-isopropenylacetate, 2b (0.5 g., 6.86 × 10⁻⁴ mole) in dry tetrahydrofuran (10 ml), cooled in an ice bath. After stirring for 5 hrs, hydrogen sulfide was bubbled through the solution, which was then filtered through celite and concentrated, to give a brown foam, whose nmr spectrum was characteristic of 1b.

The same reaction was obtained in the added presence of pyridine (0.109 g., 13.7 × 10⁻⁶ mole) during the reaction.

EXAMPLE 19
METHYL 3-PHENOXY-4-THIA-2,6-DIAZABICYCLO(3,2,0)HEPT-2-ENE-7-ONE-6-ISOPROPENYLACETATE, 1b (R = φO, R¹ = CH₃, R² = H), FROM THE REACTION OF 2b WITH ANTIMONY PENTACHLORIDE

When equimolar quantities of antimony pentachloride and 2b were mixed at 0° in methylene chloride as solvent for 15 mins, the nmr spectrum of the concentrated product showed the characteristic spectrum of 1b.

EXAMPLE 20
METHYL 3-PHENOXY-4-THIA-2,6-DIAZABICYCLO(3,2,0)HEPT-2-ENE-7-ONE-6-ISOPROPENYLACETATE, 1b (R = φO, R¹ = CH₃, R² = H) FROM THE REACTION OF 2b WITH SULFENYL IODIDES

A mixture of methyl 3-phenoxy-4,5-dithia-2,7-diazabicyclo(4,2,0)oct-2-ene-8-one-7-isopropenylacetate (200 mg., 0.55 mmoles), 2-mercaptobenzothiazole (138 mg., 0.825 mmoles) and iodine (419 mg., 1.65 mmoles) in methylene chloride (15 mls) was stirred at room temperature overnight. The reaction product was taken to dryness. The nmr spectrum of the residue showed it to be the sulfur extruded compound, methyl 3-phenoxy-4-thia-2,6-diazabicyclo(3,2,0)hept-2-ene-7-one-6-isopropenylacetate, formed in essentially quantitative yields.

In a similar manner starting from trichloroethyl 3-phenoxy-4,5-dithia-2,7-diazabicyclo(4,2,0)oct-2-ene-8-one-7-isopropenylacetate, benzhydryl 3-phenoxy-4,5-dithia-2,7-diazabicyclo(4,2,0)oct-2-ene-8-one-7-isopropenylacetate, trimethylsilyl 3-phenoxy-4,5-dithia-2,7-diazabicyclo(4,2,0)oct-2-ene-8-one-7-isopropenylacetate, trichloroethyl 3-(2',6'-dimethoxyphenyl)-4,5-dithia-2,7-diazabicyclo(4,2,0)oct-2-ene-8-one-7-isopropenylacetate, benzyl 3-(3'-phenyl-5'-methylisoxazolyl)-4,5-dithia-2,7-diazabicyclo(4,2,0)oct-2-ene-8-one-7-isopropenylacetate, and trichloroethyl 1-methoxy-3-phenoxymethyl-4,5-dithia-2,7-diazabicyclo(4,2,0)oct-2-ene-8-one-7-isopropenylacetate, it is possible to prepare trichloroethyl 3-phenoxy-4-thia-2,6-diazabicyclo(3,2,0)hept-2-ene-7-one-6-isopropenylacetate, benzhydryl 3-phenoxy-4-thia-2,6-diazabicyclo(3,2,0)hept-2-ene-7-one-6-isopropenylacetate, trimethylsilyl 3-phenoxy-4-thia-2,6-diazabicyclo(3,2,0)hept-2-ene-7-one-6-isopropenylacetate, 3-phenoxy-4-thia-2,6-diazabicyclo(3,2,0)hept-2-ene-7-one-6-isopropenyl acetic acid, trichloroethyl 3-(2',6'-dimethoxyphenyl)-4-thia-diazabicyclo(3,2,0)hept-2-ene-7-one-6-isopropenylacetate, benzyl 3-(3'-phenyl-5'-methylisoxazolyl)-4-thia-2,6-diaza-bicyclo(3,2,0)hept-2-ene-7-one-6-isopropenylacetate, and trichloromethyl 1-methoxy-3-phenoxy-methyl-4-thia-2,6-diazabicyclo(3,2,0)hept-2-ene-7-one-6-isopropenylacetate.

EXAMPLE 21

METHYL 7-PHENOXYACETAMIDO-3-METHYL-3-IODOCEPHAM-4-CARBOXYLATE FROM METHYL 3-PHENOXYMETHYL-4-THIA-2,6-DIAZABICYCLO(3,2,0)HEPT-2-ENE-7-ONE-6-ISOPROPENYLACETATE, 1b (R = $\phi$OCH$_2$, R$^1$ = CH$_3$, R$^2$ = H)

A mixture of methyl 3-phenoxymethyl-4-thia-2,6-diazabicyclo(3,2,0)hept-2-ene-7-one-6-isopropenylacetate, 1b, and iodine (1 molar equivalent) in methylene chloride were stirred at ambient temperature for 16 hrs while moist air was bubbled through. The dark brown residue after concentration was taken up in chloroform, washed with aqueous sodium thiosulfate (twice), then water (twice) and dried over magnesium sulfate. The nmr spectrum of the residue from the filtrate showed the presence of about 25% of the 3-iodocepham compound. The presence of this compound was confirmed by thin layer chromatography.

Heating the 3-iodocepham for 1 hr in benzene containing pyridine gave an about 75% yield of methyl 7-phenoxyacetamido-3-methylceph-3-ene-4-carboxylate.

EXAMPLE 22

METHYL 7-PHENOXYACETAMIDO-3-METHYL-3-IODOCEPHAM-4-CARBOXYLATE, 4 (R = $\phi$OCH$_2$, R$^2$ = H, R$^1$ = CH$_3$) FROM METHYL 3-PHENOXYMETHYL-4-THIA-2,6-DIAZABICYCLO[3,2,0]HEPT-2-ENE-7-ONE-6-ISOPROPENYLACETATE, 1 (R = $\phi$OCH$_2$, R$^2$ = H, R$^1$ =CH$_3$) USING SULFENYL IODIDES

IODINE WATER

2-Mercaptobenzothiazole (70.2 mg., 0.42 mmoles) and iodine (213 mg., 0.84 mmoles) were added to a stirred solution of methyl 3-phenoxymethyl-4-thia-2,6-diazabicyclo[3,2,0]hept-2-ene-7-one-6-isopropenylacetate (100 mgs., 0.28 mmoles) in methylene chloride (15 ml), and the mixture stirred at ambient temperature for 15 mins. Water (15 mls) was then added and the mixture stirred overnight at room temperature. The organic layer was separated, dried over magnesium sulfate, filtered and concentrated. The nmr spectrum of the residue showed the presence of about 80% of the 3-iodocepham.

In a similar manner using the thio-compounds such as thioacetamide, thioacetanilide, thiourea, N,N'-dimethylthiourea, N,N'-diphenylthiourea, t-butyl mercaptan, isopropylmercaptan, thiophenol, p-chlorothiophenol, ethyl 2-mercaptoacetate, 2-mercaptobenzooxazole, 2-mercaptobenzimidazole, 2-mercaptothiazolene, triphenylmethylmercaptan, benzylmercaptan, dimethyl disulfide, dibenzyldisulfide, di-t-butyldisulfide, di-p-tolyldisulfide, thioacetic acid and thiobenzoic acid and the following compounds;

trichloroethyl 3-phenoxymethyl-4-thia-2,6-diazabicyclo[3,2,0]hept-2-ene-7-one-6-isopropenylacetate,
p-nitrobenzyl 3-phenoxymethyl-4-thia-2,6-diazabicyclo[3,2,0]hept-2-ene-7-one-6-isopropenylacetate,
trichloroethyl 3-benzyl-4-thia-2,6-diazabicyclo[3,2,0]hept-2-ene-7-one-6-isopropenylacetate,
p-nitrobenzyl 3-benzyl-4-thia-2,6-diazabicyclo[3,2,0]hept-2-ene-7-one-6-isopropenylacetate, and
trichloroethyl 1-methoxy-3-phenoxymethyl-4-thia-2,6-diazabicyclo[3,2,0]hept-2-ene-7-one-6-isopropenylacetate, it is possible to obtain;

trichloroethyl 7-phenoxyacetamido-3-methyl-3-iodocepham-4-carboxylate,
p-nitrobenzyl 7-phenoxyacetamido-3-methyl-3-iodocepham-4-carboxylate,
trichloroethyl 7-phenylacetamido-3-methyl-3-iodocepham-4-carboxylate,
p-nitrobenzyl 7-phenylacetamido-3-methyl-3-iodocepham-4-carboxylate, and
trichloroethyl 7-methoxy-7-phenoxyacetamido-3-methyl-3-iodocepham-4-carboxylate.

EXAMPLE 23

METHYL 7-PHENOXYACETAMIDO-3-METHYLCEPH-3-EM-4-CARBOXYLATE FROM METHYL 7-PHENOXYACETAMIDO-3-METHYL-3-IODOCEPHAM-4-CARBOXYLATE, 4, (R = $\phi$OCH$_2$—, R$^2$ = H, R$^1$ = CH$_3$), USING PYRIDINE IN BENZENE A solution of methyl 7-phenoxyacetamido-3-methyl-3-iodocepham-4-carboxylate and pyridine in benzene was heated under reflux, in an oil-bath maintained at 90°. Periodically aliquots of the reaction mixture were removed and the progress of the reaction followed by analysing the nmr spectrum of the residue. The 3-iodocepham in the mixture is characterised by the C$_4$—H singlet at $\delta$4.9, the C$_6$—H doublet at $\delta$5.38 and the C$_2$—CH$_2$ quartet at $\delta$2.95; the ceph-3-em is characterised by its C$_6$—H doublet at $\delta$5.05 and its C$_2$—CH$_2$ doublet at $\delta$3.35. Any ceph-2-em produced is easily detected by its C$_3$—CH$_3$ singlet at $\delta$1.92 and its C$_2$—H signal at $\delta$6.1. In all our experiments using pyridine as the base there were no detectable amounts of the ceph-2-em isomer produced. The following table summarizes the results of experiments in which the relative amount of pyridine was varied.

TABLE 1

| Dehydroiodination of 3-Iodocepham using Pyridine in Benzene | | | |
|---|---|---|---|
| No. | Mole Ratio of Pyridine | Time of Reflux | Yield of Ceph-3-em(%)* |
| 1. | 2.5 equivalents | 0.5 hr | 45 |
| 2. | 2.5 " | 1.0 hr | 60 |
| 3. | 2.5 " | 1.5 hr | 67 |
| 4. | 5 equivalents | 0.5 hr | 50 |
| 5. | 5 " | 1.0 hr | 66 |
| 6. | 5 " | 1.5 hr | 80 |
| 7. | 5 " | 3.0 hr | ~100 |
| 8. | 10 equivalents | 0.5 hr | 60 |
| 9. | 10 " | 1.0 hr | ~100 |
| 10. | 10 " | 1.5 hr | 100 |

*There was no detectable trace of any ceph-2-em isomer in any of these experiments.

EXAMPLE 23

METHYL 7-PHENOXYACETAMIDO-3-METHYLCEPH-3-EM-4-CARBOXYLATE FROM METHYL 7-PHENOXYACETAMIDO-3-METHYL-3-IODOCEPHAM-4-CARBOXYLATE, 4 (R = $\phi$OCH$_2$—, R$^2$ = H, R$^1$ = CH$_3$) USING PYRIDINE ALONE Methyl 7-phenoxyacetamido-3-methyl-3-iodocepham-4-carboxylate (100 mg) was dissolved in pyridine d$_5$ (0.5 ml) and the reaction monitored by running an nmr spectrum on the sample periodically. After about 15 mins at ambient temperature there was about 50% conversion to the ceph-3-em, and after 2 hrs the reaction was complete. The nmr spectrum did not change after a 24-hour period and again no detectable amount of the ceph-2-em isomer was observed.

We claim:

1. The process of desulfurization for preparing a compound of the formula:

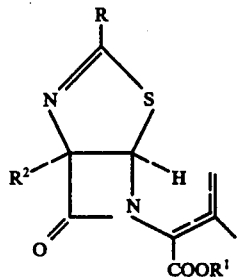

wherein:

R stands for phenoxyloweralkyl, phenylthioloweralkyl, benzyl, lower alkyl, phenyl, methylisoxazolyl, a-aminobenzyl and protected derivatives thereof selected from the group consisting of N-benzyloxycarbonyl, N-trichloroethoxycarbonyl, and N-methozymethozycarbonyl, 4-amino-r-carboxy-1-butyl, $R^3O-$, $R^3S-$, and $R^3R^4N-$ where $R^3$ is lower alkyl, phenyl, or phenylloweralkyl, $R^4$ is hydrogen or radical $R^3$, $R^2$ is hydrogen or methoxy;

$R^1$ is hydrogen, lower alkyl, loweralkoxymethyl, phenoxymethyl, 2,2,2-trichloroethyl, benzyl, p-nitrobenzyl, benzhydryl, or trimethylsilyl, which comprises the step of contacting a dithiazeneazetidinone of the formula:

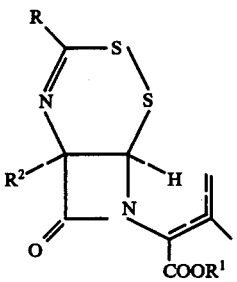

R, $R^1$ and $R^2$ being the same as defined previously with iodine.

2. The process of claim 1 wherein the iodine is generated in situ from $R^3SH-I_2$ wherein $R^3$ is defined in claim 1.

3. The process of claim 1 wherein the iodine is generated in situ from benzothiazole-2-sulfenyl iodide.

4. The process of claim 1 which is carried out in the presence of an inert organic solvent.

5. The process of claim 1 which is carried out in the presence of thiosulfate.

6. The process of claim 5 wherein R is phenoxymethyl.

7. The process of claim 1 which is carried out in the absence of thiosulfate.

8. The process of claim 7 wherein R is phenoxy.

9. The process of claim 1 which comprises the additional step of removing excess iodine with a thiosulfate.

10. The process of claim 1, wherein methyl 3-phenoxymethyl-4,5-dithia-2,7-diazabicyclo[4,2,0]oct-2-ene-8-one-7-isopropenylacetate is treated with iodine to form the 3-phenoxy-4-thia-2,6-diazabicyclo[3,2,0]hept-2-ene-7-one-6-isopropenylacetate.

11. The process of claim 1, wherein methyl 3-phenoxy-4,5-dithia-2,7-diazabicyclo[4,2,0]oct-2-ene-8-one-7-isopropenylacetate is treated with iodine to form the methyl 3-phenoxy-4-thia-2,6-diazabicyclo[3,2,0]hept-2-ene-7-one-6-isopropenylacetate.

12. The process of claim 1, wherein methyl 3-phenoxy-4,5-dithia-2,7-diazabicyclo(4,2,0)oct-2-ene-8-one-7-isopropenyl acetate is treated with iodine in presence of 2-mercaptobenzothiazole to form methyl 3-phenoxy-4-thia-2,6-diazabicyclo(3,2,0)hept-2-ene-7-one-6-isopropenylacetate.

* * * * *